United States Patent

Teissier et al.

Patent Number: 5,672,764
Date of Patent: Sep. 30, 1997

[54] SELECTIVE ALDOLIZATION OF ACETONE TO DIACETONE ALCOHOL BY A SOLID BASIC CATALYST

[75] Inventors: Rémy Teissier, Francheville; Didier Tichit, Montpellier Cedex; François Figueras; Jacques Kervennal, both of Lyons, all of France

[73] Assignee: Elf Atochem S.A., Puteaux, France

[21] Appl. No.: 584,900

[22] Filed: Jan. 5, 1996

[30] Foreign Application Priority Data

Jan. 6, 1995 [FR] France ................................. 95 00094

[51] Int. Cl.$^6$ ................................................. C07C 45/45
[52] U.S. Cl. .......................... 568/388; 568/390; 502/341
[58] Field of Search ...................... 568/388, 390; 502/341

[56] References Cited

PUBLICATIONS

Kozo Tanabe et al; "Addition of metal ions—Acetone"; Applied Catalysis;48; pp. 63–70, 1989.
G. Mascolo et al; "A new synthesis—hydroxides"; Mineralogical Magazine; 43; pp. 619–621, 1980.

Primary Examiner—C. Warren Ivy
Assistant Examiner—Sreeni Padmanabhan
Attorney, Agent, or Firm—Pennie & Edmonds

[57] ABSTRACT

The aldolization is characterized by the use of a solid basic catalyst which has the following general formula $$[(Mg^{2+})_{1-x}(Al^{3+})_x(OH^-)_2]^{x+}[(OH^-)_x(H_2O)_n]^{x-} \qquad (II)$$

wherein $0.20 \leq x \leq 0.33$ and n has a value of less than 1. This catalyst has a defined crystal structure similar to that of hydrotalcite or, alternatively, of meixnerite. Also disclosed are processes for the preparation of the catalyst.

4 Claims, No Drawings

SELECTIVE ALDOLIZATION OF ACETONE TO DIACETONE ALCOHOL BY A SOLID BASIC CATALYST

FIELD OF THE INVENTION

The present invention relates to the manufacture of diacetone alcohol by basic catalysis and more precisely by heterogeneous basic catalysis.

BACKGROUND OF THE INVENTION

G. S. Salvapati et al., *Journal of Molecular Catalysis*, vol. 54, pp. 9–30, (1989), have published a review on the complex reactions and the many products which may be obtained by self-condensations and trans-condensations in basic medium of ketone products derived from acetone.

Acetone leads firstly, via an equilibrium reaction, to diacetone alcohol (DA). This product may either dehydrate to give one molecule of mesityl oxide (MO) and one molecule of water, or may react with a third molecule of acetone to give a triacetone dialcohol (TAD).

Craven E. C., *J. Appl. Chem.*, vol. 13, pp. 71–77, (1963), had already determined that, in the equilibrium reaction, the content of DA (in % by weight) at equilibrium depended on the reaction temperature $t_r$: 0° C. (23.1%), 10° C. (16.9%), 20° C. (12.1%), 30° C. (9.1%).

Moreover, an industrial process for the manufacture of DA by catalysis using sodium hydroxide (2.5 milli-equivalents/kg of acetone) is known. This homogeneous process has many drawbacks. Before distilling the DA, the sodium hydroxide must be removed by neutralization using phosphoric acid, precipitation of the sodium phosphate, and filtration. However, after these treatments, sodium phosphate remains in the mixture containing the DA, this remaining phosphate gradually encrusting the distillation columns. Consequently, the distillation must be stopped regularly in order to clean the columns, thereby substantially decreasing the production efficiency of the industrial production unit.

A basic heterogeneous catalysis by a solid basic catalyst which is readily separable from the organic phase would make it possible to simplify the process and to do away with the effluents originating from neutralization of the sodium hydroxide.

Geng Zhang et al., *Applied Catalysis*, vol. 36, pp. 189–197, (1988), have studied the aldolization of acetone catalysed by solid basic catalysts such as magnesium oxide (MgO), calcium oxide (CaO), strontium oxide (SrO), barium oxide (BaO), lanthanum III oxide ($La_2O_3$), and zirconium oxide ($ZrO_2$). These authors have found that the activities of these catalysts based on the same specific surface unit were in the order: $BaO>SrO>CaO>MgO>La_2O_3>ZrO_2$. Furthermore, for MgO, the addition of water and ammonia by pre-adsorption led to a marked increase in activity and in selectivity in the production of DA.

Kozo Tanabe et al., *Applied Catalysis*, vol. 48, 63–70, (1989), studied the addition of metal cations to magnesium oxide in order to obtain a catalyst for the aldolization of acetone. The influence of the $Na^+$, $K^+$, $Rb^+$, $Cs^+$, $Al^{3+}$, $Mn^+$, $Fe^{3+}$, $CO^{3+}$, $Ni^{2+}$, $CU^{2+}$, $Zn^{2+}$ and $Zr^{4+}$ cations was studied. These authors noticed that the $Na^+$, $Zr^{4+}$ and $Zn^{2+}$ cations increased the catalytic activity efficiently for a weight content of 0.5 to 1% of the metal cation. The addition of water in suitable amounts increased both the activities and the selectivities of these MgO catalysts doped with these cations. On the other hand, these authors demonstrated that the addition of any concentration of $Al^{3+}$ resulted in a decrease in the activity. This decrease, indicated in FIG. 3 of the article, went in the same direction as the increase in the content of $Al^{3+}$. The range studied for $Al^{3+}$ varied between 0% and about 3% of $Al^{3+}$ by weight.

G. Mascolo et al., *Mineralogical Magazine*, 1980, vol. 43, pp. 619–21, (1980), have described a novel synthesis of Mg-Al double hydroxides (DH) having a low content of $CO_2$ (0.8–1%) and being of general formula (I):

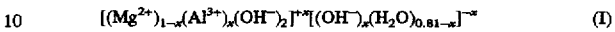
$[(Mg^{2+})_{1-x}(Al^{3+})_x(OH^-)_2]^{x+}[(OH^-)_x(H_2O)_{0.81-x}]^{-x}$ (I)

with $0.23 \leq x \leq 0.33$

These DHs have a crystal structure similar to those of natural hydrotalcite or manasseite, with a rhombohedric crystal lattice.

If $x_{Mg}$ is defined by the molar ratio: $x_{Mg}=Mg/(Mg+Al)$, the composition range of the pure DH exists for values of $x_{Mg}$ such that $0.67 \leq x_{Mg} \leq 0.77$.

The parameters a and c of the unit crystal lattice for the limiting compositions are:

a=3.038 Å c=22.6 Å, for the limiting composition rich in $Al^{3+}$, and a=3.054 Å c=23.4 Å, for the limiting composition rich in $Mg^{2+}$.

These DHs would thus be composed, like natural hydrotalcite, of positively charged layers of the brucite type of formula $[Mg_{1-x}Al_x(OH)_2]$ and of inter-layers consisting of hydroxyls (OH—) and of water molecules.

In the family of DHs, a natural ore is known, meixnerite of formula $Mg_6Al_2(OH)_{18} \cdot 4H_2O$, containing less than 2% of $CO_2$ but which avidly absorbs atmospheric $CO_2$ during any grinding of the ore in air.

The formula of meixnerite, expressed as a specific type of case of the general formula (I), is:

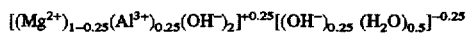
$[(Mg^{2+})_{1-0.25}(Al^{3+})_{0.25}(OH^-)_2]^{+0.25}[(OH^-)_{0.25}(H_2O)_{0.5}]^{-0.25}$ i.e., x=0.25.

The DHs of G. Mascolo et al. are prepared from MgO obtained by calcination of basic magnesium carbonate at 650° C. for 6 hours and of Merck alumina gel. These two components are introduced in a specific molar ratio $x_m$ and are suspended in distilled water, in a closed Teflon container, with stirring, for one week at 80°±1° C. The suspension is then filtered in the absence of $CO_2$ and, lastly, the solid collected is dried over silica gel.

According to Allmann, *Fortschr. Mineral*, vol. 48, pp. 24–30, (1971), in the compounds of the hydrotalcite type containing anions and water molecules between the charged layers of the brucite type of formula: $[Mg_{1-x}Al_x(OH)_2]$, x has a value such that $0.20 \leq x \leq 0.33$.

SUMMARY OF THE INVENTION

It has been found by the present invention that the DHs of G. Mascolo et al. constitute excellent catalysts for the selective aldolization of acetone to DA. Furthermore, a novel process for the synthesis of the compounds of general formula (II) in which x has a value such that $0.20 \leq x \leq 0.33$ has been developed.

More precisely, the present invention provides a process for the selective aldolization of acetone to diacetone alcohol which comprises the step of reacting acetone in the presence of a solid basic catalyst which has the general formula:

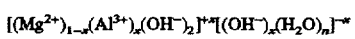
$[(Mg^{2+})_{1-x}(Al^{3+})_x(OH^-)_2]^{x+}[(OH^-)_x(H_2O)_n]^{-x}$ wherein $0.20 \leq x \leq 0.33$ and $n<1$.

The present invention also provides a process for the preparation of the catalyst as described above, which process comprises the steps: a) calcining a hydrotalcite in which x has a value such that $0.20 \leq x \leq 0.33$ at a temperature below 800° C. in order to obtain a mixed oxide of magnesium and of aluminium, and b) rehydrating the mixed oxide thus obtained with water in the absence of $CO_2$.

DESCRIPTION OF THE PREFERRED EMBODIMENTS

The present invention lies firstly in a process for the selective aldolization of acetone to diacetone alcohol (DA) in the presence of a solid basic catalyst, characterized in that the catalyst has the general formula (II):

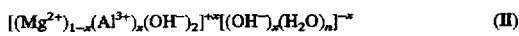

(II)

with $0.20 \leq x \leq 0.33$.

When n has a value of less than 1, this catalyst has a defined crystalline structure similar to that of hydrotalcite or, alternatively, of meixnerite. Preferably, n has a value such that $0.5 \leq n \leq 0.75$. Advantageously, n has a value equal to or in the region of $0.81-x$ and includes the value $n=0.5$ of meixnerite for which x has the value 0.25.

The present invention also proposes a process in which a mixed oxide of magnesium and of aluminium is rehydrated, in the absence of $CO_2$. More precisely, the invention provides a process for the preparation of the catalyst of general formula (II), characterized in that it includes the following steps:

a) a hydrotalcite in which x has a value such that $0.20 \leq x \leq 0.33$, is calcined at a temperature below 800° C., in order to obtain a mixed oxide of magnesium and of aluminium, and b) the mixed oxide thus obtained is rehydrated with water in the absence of $CO_2$.

The very basic catalysts (II) have a natural tendency to become carbonated in the presence of air. Their preparation and their use must take place in a medium free of carbon dioxide. The partial replacement of the anion $(OH)^-$ by the carbonate anion $CO_3^{2-}$ only partially decreases the catalytic properties of the catalyst (I). On the other hand, the hydrotalcite of formula:

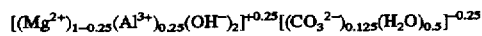

no longer has an appreciable catalytic property in the aldolization of acetone to DA.

EXAMPLES

The present invention will be even better understood by virtue of the following experimental section:

1) Preparation of the catalysts of general formula (II)

In addition to the Mascolo et al. preparation reported above, two synthetic processes were used:

Starting with a hydrotalcite synthesized according to S. Myata, *Clays and Clay Minerals*, vol. 28, pp. 50–56 (1980).

Starting with a double oxide of magnesium and of aluminium marketed by the Japanese company Kyowa under the reference KW 2000.

1.1) Starting material: hydrotalcite 1.1) Synthesis of hydrotalcite

This synthesis is carried out according to the method of S. Myata by mixing, in alkaline medium, a solution of $MgCl_2$ with a solution of $AlCl_3$. After filtration and drying, a hydrotalcite with an Mg/Al molar ratio of 2.27 (i.e. $x=0.306$) is obtained. The specific surface measured by the BET method is 80 $m^2/g$.

1.1.2) Exchange with carbonate

The product obtained above is exchanged twice as follows: to a solution of 0.69 g of $Na_2CO_3$ in 100 ml of distilled water are added two grams of hydrotalcite. The suspension is maintained at 80° C. for three hours with stirring. It is filtered, followed by washing twice with water. A second exchange is carried out in the same manner. A solid is obtained which contains no detectable chloride by potentiometry.

1.1.3) Calcination

The above exchanged solid is calcined in dry air according to the following heating program:

raising to 450° C. over 1 hour or more, plateau at 450° C. for 10 hours, cooling while flushing with $CO_2$-free dry air.

The weight of the calcined solid represents 60 to 65% of the weight of initial solid.

1.1.4) Activation

At room temperature, the dry air is replaced by a $CO_2$-free gas such as nitrogen which has been passed beforehand through a saturator filled with water. For an initial weight of 5 g of hydrotalcite, a flow rate of 5.5 liters of wet nitrogen is sent through for 16 h, equivalent to a total volume of 18 l of wet nitrogen per gram. The solid obtained of general formula II, in which x has the value 0.306, is immediately tested in the catalytic test which will be described later.

1.2) Starting material: KW 2000

This double oxide has the following characteristics:

| | |
|---|---|
| Chemical formula: | 4.5 MgO—$Al_2O_3$ (x = 0.3077) |
| Apparent density: | 44 ml/10 g |
| Appearance: | fine, white, odourless powder |
| BET (M2/g): | 172 |
| Mean particle size: | 70 μm |
| Dehydrating property: | absorbs a maximum of 70–80 parts of water per 100 parts of KW 2000. |

1.2.1) Hydration by water in the liquid phase

Six grams of KW 2000 are added with stirring to 200 ml of decarbonated water (water which is deionized and then boiled). The mixture is left for three hours and the water is then evaporated off under vacuum at about 40° C. 9 g of solid are obtained, which product is stored overnight in the absence of $CO_2$, before being ground rapidly, still in the absence of contact with $CO_2$. A divided solid of general formula (II) in which x has the value 0.3077 and which has a crystal structure of the hydrotalcite type or of the meixnerite type is thus obtained.

1.2.2) Hydration by water in the vapour phase

Ten grams of KW 2000 are arranged in a thin layer in a crystallizing dish. The crystallizing dish is introduced into a desiccator into the base of which about 20 g of water have been poured, after the desiccator has been flushed beforehand with nitrogen in order to remove any trace of $CO_2$. The solid is left in this water-saturated atmosphere for at least 3 days. After five days, the solid weighs 13.3 g.

A solid in the form of a powder of general formula (II) in which x has the value 0.3077 and which has the same crystal structure as the solid obtained in 1.2.1) is thus obtained.

2) Catalytic testing 100 g of commercial acetone (Aldrich, ref. 17,912-4) are introduced into a stirred 500 ml reactor fitted with a reflux condenser, a system for placing under an inert atmosphere of nitrogen, and a jacket allowing thermostatic control of the reactor by circulation of a heat-exchange fluid. The acetone is cooled to 0° C. with stirring, while flushing the head space of the reactor with nitrogen. When the temperature is stabilized, the catalytic charge is introduced, avoiding as much as possible any contact of this charge with air. The mixture is allowed to react with stirring. A sample is withdrawn at regular intervals and analysed by gas chromatography (GC).

Since the reaction medium is composed of an organic liquid and of the solid basic catalyst, it is very easy to separate these two phases, for example by settling or filtration in the absence of $CO_2$, and hence in the absence of air. The formation of diacetone alcohol (DA), mesityl oxide (MO) and triacetone dialcohol (TAD) is thus monitored.

The characteristics of the GC analysis are as follows:

Hewlett-Packard HP5-(Si8) capillary column 25 m in length and 0.55 nun in diameter Flame ionization detection (FID)

Carrier gas: $N_2$ 6 ml/min

Column temperature: 4 min at 60° C., then 6° C./min up to 180° C.

Injector: temperature 150° C.

Detector: temperature 200° C.

Internal standard: xylene 2.1) Example 1

Test using the catalyst 1.1.4 (×0.306). This example is featured in Table I.

TABLE I

| DURATION IN HOURS | DA % BY WEIGHT | TAD % BY WEIGHT | MO % BY WEIGHT |
|---|---|---|---|
| 0 | 0 | 0 | 0 |
| 1 | 16.5 | 0.6 | 0 |
| 2 | 21 | 0.8 | 0 |
| 3 | 22.9 | 0.85 | 0 |
| 4 | 24.6 | 0.9 | 0 |

2.2) Comparative Example 2

By way of comparison, with sodium hydroxide. (NaOH) at a concentration of 2.5 m.eq/kg of acetone, in replacement for the heterogeneous catalyst of Example 1, the results given below in Table II are obtained under the same experimental conditions.

TABLE II

| DURATION IN HOURS | DA % BY WEIGHT |
|---|---|
| 0 | 0 |
| 1 | 13 |
| 2 | 14.5 |
| 3 | 18 |
| 4 | 18.5 |

2.3) Comparative Example 3

By way of comparison, the calcined solid 1.1.3 is used in the catalytic test. The results are featured in Table III.

TABLE III

| DURATION IN HOURS | DA % BY WEIGHT |
|---|---|
| 0 | 0 |
| 1 | 0.8 |
| 2 | 1.4 |
| 3 | 2 |
| 5 | 2.9 |
| 24 | 7 |

2.4) Comparative Example 4

Instead of starting with hydrotalcite according to preparation 1.1), MgO was used. This MgO was calcined according to 1.1.3) and then activated according to 1.1.4). This type of catalyst corresponds to those described by Geng Zhang et al. (see above). The test is performed under the same general conditions. The results are featured in Table IV.

TABLE IV

| DURATION IN HOURS | DA % BY WEIGHT | TAD % BY WEIGHT |
|---|---|---|
| 1 | 4.5 | — |
| 2 | 6.8 | 0.2 |
| 3 | 8.5 | 0.25 |
| 8 | 13 | — |
| 24 | 19 | 0.6 |

2.5-2.6-2.7) Examples 5, 6, and 7 respectively

The amount of wet nitrogen in the activation 1.1.4) of calcined hydrotalcite was varied These activations are performed at the same temperature of 20° C. The flow rate of gas, and thus the amount of wet nitrogen used per gram of calcined solid, is varied. The catalysts obtained are defined below by a coefficient of activity $C_a$, this being equal to the mass of DA formed during the first hour of the test, divided by the mass of the catalyst used. The results are given in Table V.

TABLE V

| EXAMPLE | $N_2$ WET IN LITERS PER G OF CATALYST | $C_a$ |
|---|---|---|
| 5 | 5 | 0.2 |
| 6 | 11 | 1.5 |
| 7 | 25 | 3.4 |

2.8) Example 8

The solid catalyst obtained in 1.2.1) by hydration of KW 2000 by water in the liquid phase is tested in the following way:

4.5 g of this ground solid are introduced into 100 g of acetone cooled beforehand to 0° C. and under a nitrogen atmosphere. The mixture is left to react with stirring. After reaction for one hour, 13.75 g of DA are obtained, equivalent to a coefficient $C_a$ equal to 3.

2.9) Example 9

The solid catalyst obtained in 1.2.2) by hydration of KW 2000 by water in the vapour phase is tested in the same way as in Example 8 above, but with an amount of solid of 2.9 g. The coefficient of activity $C_a$ is equal to 4.1.

2.10) Example 10

The catalyst of Example 1 was collected by rapid filtration and then recycled 7 times in the test defined above. The results are featured in Table VI.

TABLE VI

| NUMBER OF RECYCLES | $C_a$ |
|---|---|
| 1 | 3.6 |
| 2 | 3.7 |
| 3 | 3.3 |
| 4 | 3.3 |
| 5 | — |
| 6 | 3.6 |
| 7 | 3.7 |

These 7 recycles do not lead to any loss of activity for the catalyst.

2.11) Example 11

The catalyst of Example 6 was collected by rapid filtration and then dried overnight in a ventilated oven at 100° C. It was then subjected to calcination according to 1.1.3), then activated according to 1.1.4) and, lastly, subjected to the test. Its coefficient of activity $C_a$ is 3.8.

In conclusion, the above examples show that the catalysts according to the invention allow very good conversion into DA. The degree of conversion is able to equal the thermodynamic equilibrium value at 0° C., with excellent selectivity (at least 97%). Furthermore, these catalysts retain their activity on recycling.

We claim:

1. A process for the selective aldolization of acetone to diacetone alcohol which comprises the step of reacting acetone in the presence of a solid basic catalyst which has the general formula:

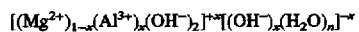

wherein $0.20 \leq x \leq 0.33$ and $n<1$.

2. The process of claim 1, wherein $0.5 \leq n \leq 0.75$.

3. The process of claim 1, wherein n has a value of about $0.81-x$.

4. A process for the preparation of the catalyst of general formula:

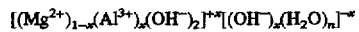

wherein $0.20 \leq x \leq 0.33$ and $n<1$, which process comprises the steps:

a) calcining a hydrotalcite in which x has a value such that $0.20 \leq x \leq 0.33$ at a temperature below 800° C. in order to obtain a mixed oxide of magnesium and of aluminium, and b) rehydrating the mixed oxide thus obtained with water in the absence of $CO_2$.

* * * * *